United States Patent [19]
Wiese

[11] Patent Number: 5,019,516
[45] Date of Patent: May 28, 1991

[54] LEAD EXTRACTION AND ANALYSIS
[75] Inventor: Patrick M. Wiese, Loveland, Colo.
[73] Assignee: Hach Company, Loveland, Colo.
[21] Appl. No.: 484,416
[22] Filed: Feb. 23, 1990

Related U.S. Application Data

[63] Continuation-in-part of Ser. No. 364,652, Jun. 9, 1989, abandoned.

[51] Int. Cl.$^5$ .............................................. G01N 21/00
[52] U.S. Cl. ..................... 436/77; 436/164; 436/171; 436/178; 436/182; 210/725; 210/778; 210/797; 210/912
[58] Field of Search ............. 210/725, 778, 797, 912; 436/73, 77, 164, 171, 177, 178, 182

[56] References Cited

U.S. PATENT DOCUMENTS

| | | | |
|---|---|---|---|
| 3,790,370 | 2/1974 | Lalancette | 75/108 |
| 4,076,618 | 2/1978 | Zeblisky | 210/30 R |
| 4,908,137 | 3/1990 | Chen | 210/679 |

FOREIGN PATENT DOCUMENTS

| | | |
|---|---|---|
| 2230594 | 1/1973 | Fed. Rep. of Germany. |
| 2263047 | 7/1973 | Fed. Rep. of Germany. |

OTHER PUBLICATIONS

Pilipenko, A. T. et al. "Extraction-Atomic Absorption Determination of Trace Elements in Natural Waters," CA 96(8):57465s.
Fritz, J. S. et al. "Quantitative Analytical Chemistry", Boston, Mass.: Allyn and Bacon Inc. 1979, pp. 104–105.
CA 99(6):47124c "Appl. of the ion-exchager Cellex P . . . ", Fresenius Z. Anal. Chem., 315(2) pp. 126–131, 1983.
Minczewski, J. et al. "Separation and Preconcentration Methods in Inorganic Trace Analysis", New York: Ellis Harwood Limited, 1982.

*Primary Examiner*—David Lacey
*Assistant Examiner*—David Redding
*Attorney, Agent, or Firm*—Dean P. Edmundson

[57] ABSTRACT

Techniques are described for extracting lead from a sample of potable water and analyzing for the amount of lead so extracted. A complexing agent is added to the water to form a complex with the lead. The water is then contacted with unmodified cellulosic or siliceous material on which the lead complex is retained. The complexed lead can be removed from the cellulosic or siliceous material with a weak acid. The amount of lead in the sample can be readily determined colorimetrically.

11 Claims, No Drawings

LEAD EXTRACTION AND ANALYSIS

CROSS-REFERENCE TO RELATED APPLICATION

This application is a continuation-in-part of my co-pending application Ser. No.07/364,652, filed June 9, 1989 now abandoned.

FIELD OF THE INVENTION

This invention relates to techniques for extraction of lead from water (e.g., drinking water). More particularly, this invention relates to extraction of lead from water followed by quantitative analysis of the lead.

BACKGROUND OF THE INVENTION

Lead is a toxic metal which can be harmful to human health even at low exposure levels. Lead is sometimes referred to as a cumulative toxin because the lead concentrates in the body. Young children, infants, and fetuses are particularly vulnerable to lead because the physical and behavioral effects of lead occur at lower exposure levels in children than in adults. Overexposure to lead can permanently impair a child's mental and physical development.

Comparatively low levels of exposure have been linked to damage to the central and peripheral nervous system, learning disabilities, shorter stature, impaired hearing, and impaired formation and function of blood cells. At its worst, lead poisoning can result in stupor, coma, kidney damage, or severe brain damage.

Lead in drinking water (i.e. potable water) can be a significant contributor to overall exposure to lead, particularly for infants whose diet consists of liquids made with water, such as baby food formula. Consequently, there is a great need to test potable water to determine whether such water contains less than the 5 parts per billion (ppb) maximum limit proposed by the EPA for public drinking water and to check for less than 10 parts per billion on firstdraw samples at the point of use. One ppb is equal to one microgram per liter.

Although it is possible to analyze water samples using atomic absorption (i.e. spectroscopic analysis) techniques, such techniques are cumbersome and subject to error due to interferences. For example, the sample must first be prepared in order to convert organic forms of lead to inorganic forms, to minimize organic interferences, and to convert the sample to a suitable solution for analysis. Then the prepared sample is placed into a graphite tube furnace where the sample is slowly evaporated to dryness, charred (ashed) and then atomized. The absorption of hollow cathode radiation during atomization is proportional to the lead concentration.

The atomic absorption method is subject to various disadvantages. For example, it requires the use of an atomic absorption spectrophotometer and a graphite furnace. It also requires a trained operator, a lengthy set-up time, and the equipment required is extremely expensive. Thus, this technique is not suitable for use in the field. Rather it must be used in the laboratory.

Also, the atomic absorption method is subject to various types of interference. The long residence time and high concentrations of the atomized sample in the optical path of the graphite furnace can result in severe physical and chemical interferences. Furnace parameters must be optimized to minimize such effects. Lead analysis can also suffer from severe nonspecific absorption and light scattering caused by matrix components during atomization. Simultaneous background correction must be employed to avoid erroneously high results. Also, if the analyte is not completely volatilized and removed from the furnace during atomization, memory effects will occur, thereby requiring cleaning of the tube by operating the furnace at higher atomization temperatures. Further, the presence of sulfate can suppress lead absorbance, thereby requiring the use of a lanthanum releasing agent.

It is also possible to analyze potable water for lead using ammoniacal citrate-cyanide reducing solution, followed by extraction with dithizone in chloroform. The final solution can then be analyzed photometrically. This method is not reliable for detecting low levels of lead in water. Also, the use of solvents and cyanide presents a disposal problem. Thus, this method is not readily useful except in a laboratory environment.

The use of special ion exchange resins, such as the phosphoryl-modified cellulose based "Cellex P", has been described, but such use requires very carefully controlled flow rates for passing fluid solutions through the material in order to retain the metals on the resins. Such materials are of small particle size (measured in microns). Oftentimes the flow rates are extremely slow (e.g., 1–5 mL per minute) which makes the analysis very time consuming. Also, the required elution step involves the use of strong acids or specific flow rates to separate the metals. As a result, the use of ion exchange resins has attendant drawbacks.

Solvent extractions have also been used in separation of lead ions from solution. Such extractions involve the use of amine complexing agents and toxic or flammable reagents. Also, further concentration, drying or ashing of the extract is often necessary before analysis can be completed.

There has not heretofore been described a simple, effective, rapid, and safe technique for extracting lead ions from potable water and then analyzing to determine the amount of lead extracted.

SUMMARY OF THE PRESENT INVENTION

In accordance with the present invention there is provided a method for extracting lead from a sample of potable water and then analyzing to determine the amount of lead which has been extracted. In one embodiment, the method comprises:

(a) adjusting the pH of the water sample to less than about 4;

(b) adding to the water sample a quantity of complexing agent sufficient to form a complex with the lead present in the sample; wherein the complexing agent comprises a dipolar compound;

(c) adjusting the pH of the water to the range of about 6 to 10;

(d) passing the sample through cellulosic or siliceous material at a rate of about 10 to 200 mL. per minute (preferably at a rate of about 20 to 100 mL. per minute and, more preferably, at a rate of about 50 to 100 mL. per minute); wherein the complex is retained on the surface of the cellulosic or siliceous material.

Then the lead complex can be easily removed from the cellulosic or siliceous material (e.g., with weak acid) and quantitatively analyzed to determine the amount of lead present. For example, colorimetric methods may be used simply and easily to determine the amount of lead present.

Preferably the cellulosic or siliceous material is in the form of fibers having a length of at least about one inch or more. Other forms may be used so long as there is high surface area and the material does not pack so tightly that water will not flow through it at the high flow rate described herein. The flow rate of the water through the fibrous material is not required to be constant, so long as the flow rate is in the range of about 10 to 200 mL. per minute.

The technique of this invention is rapid, reliable, safe, and very simple to use in the field. The technique does not require laboratory conditions or expensive equipment. It does not require extraction with organic solvent, nor is cyanide used. No reagent disposal problem is presented. Consequently, the technique can be used on-site to obtain accurate analysis of potable water anywhere.

Further, the technique of this invention is not affected by the interferences normally found in potable water. The technique is inexpensive and easy to use. Non-technical personnel are able to perform the testing and obtain accurate and reliable results.

The simplicity of the technique of the present invention enables the use of standards and proof of accuracy techniques to be performed in the field to verify testing results. These advantages have not heretofore been available with other lead testing techniques.

DETAILED DESCRIPTION OF THE INVENTION

A sample of potable water to be tested in accordance with the present invention can be collected in accordance with conventional sampling techniques. The size of the sample may vary. Generally speaking, a 100 milliliter sample of potable water is sufficient for the technique of this invention.

To the sample of potable water there is first added an acid to adjust the pH to a level below about 4 (preferably to a level less than about 2). This can be done by adding an acid such as nitric, hydrochloric, acetic, or phosphoric, for example.

Then there is added a complexing agent in an amount sufficient to form a complex with the lead present in the water sample. The complexing agent is a dipolar compound, preferably including an amine group and an electronegative group (e.g. hydroxyl, carboxylic acid, or sulfonic acid). The complexing agent is added in great excess so that all of the lead present in the water sample becomes complexed. In other words, the number of moles of complexing agent must be equal to or greater than the number of moles of lead present in the sample.

Preferred complexing agents include: tris-(hydroxymethyl) aminomethane; glycine; 2,2-bis(hydroxymethyl)-2,2',2'''-nitriloethanol; and 4-morpholineethanesulfonic acid.

After the complexing agent has been added and the water sample has been adequately mixed, the water pH is preferably adjusted to the range of about 6 to 10 (and even more preferably to a range of about 6.7 to 7.1). If the complexing agent is not alkaline itself then the pH of the sample can be readily adjusted using sodium or potassium hydroxide (lead-free). The complexing agent is preferably added to the water sample first so as to prevent the formation of lead hydroxide which would occur if the hydroxide was added prior to addition of the complexing agent.

Then the prepared sample is placed in contact with chemically unmodified cellulosic or siliceous material for a time and under such conditions that the complexed lead becomes adhered to or retained on the surface of such material. Preferably the water sample is simply poured through the material by means of gravity. The flow rate of the water through the material should be relatively rapid (e.g., about 10 to 200 mL. per minute, and preferably is in the range of about 20 to 100 mL. per minute and, more preferably, is in the range of about 50 to 100 mL. per minute).

As referred to herein, and as is well understood in the art, the term "unmodified" is intended to mean cellulosic or siliceous materials of the same chemical composition as is present in their naturally occurring state. Modified or chemically functionized materials which have been chemically reacted or changed in order to modify the basic chemical composition, as is the case of cellulose based ion exchange resins, are not required in the techniques of this invention but may be used so long as the flow rate of water through the material is at least 10 mL. per minute (preferably at least 20 mL. per minute, and more preferably at least about 50 mL. per minute).

The preferred type of cellulosic material used comprises unmodified cotton fibers (e.g. cotton balls). It is also possible to use wood fibers. The preferred type of siliceous material used comprises glass wool. This material includes an abundance of unmodified glass fibers.

The fibers have a length of at least about one inch. Longer fibers, of course, may also be used.

The cellulosic or siliceous material to be used is preferably contained in a column (e.g a syringe barrel) which may be connected to a container at its lower end. A beaker may be used to collect water passing through the column. Since the lead has been extracted from the water in the column, there is no need to retain this collected water.

When the water is passed through the cellulosic or siliceous material the complexing agent is attracted to the surface of the material so that the lead ions (which are complexed with the complexing agent) are extracted from the water sample. The alkali and alkaline earth cations are not complexed and accordingly pass through the cellulosic or siliceous material. Some other heavy metals such as copper iron and zinc which may be present in the water are only partially retained during this step. Anions such as chlorides, nitrates and sulfates are not retained on the cellulosic or siliceous material.

It is believed that the weakly cationic complexes are adsorbed on or electrically attracted to the negatively charged hydroxyl groups on the cellulosic or siliceous material.

Then the lead can be eluted from the cellulosic or siliceous material by means of a weak acid. This is accomplished by pouring the weak acid through the material and collecting it in a sample cell or reaction vessel. Iron and other insoluble metal particles which may have been retained on the cellulosic or siliceous material are not removed by the weak acid solution.

The type of acid used for elution of the lead is preferably 0.04N nitric acid. Other types of acids could also be used, such as hydrochloric, acetic, phosphoric, etc.

After the lead has been eluted with the acid, the reaction mixture is neutralized with sodium hydroxide and additional complexing agent. Preferably the pH is adjusted to the range of about 8.8 to 9.0 to facilitate reaction of the lead with a color indicator, described below.

Then a color indicator is added to the lead solution. A preferred color indicator to be used is meso-tetra(4-N-methylpyridyl) porphine tetratosylate. Another useful indicator which may be used is meso-tetra(3-N-methylpyridyl) porphine tetratosylate.

The lead solution is then placed in a colorimeter. Absorbance is measured on a spectrophotometer at 477 nm. The lead-indicator complex is then destroyed with EDTA, after which the absorbance is measured again. The absorbance difference is directly proportional to the amount of lead present in the solution. The absorbance due to the lead-indicator complex is first measured. The EDTA forms a stronger complex than the lead-indicator and accordingly destroys or pulls away the lead from the indicator. The absorbance is then read again to compensate for the background unreacted indicator.

Preferably a 100 ml. sample of potable water is used for testing. The pH is initially adjusted to less than about 2 with nitric acid (preferably containing 10% potassium nitrate as preservative), after which 2.0 ml. of the complexing agent is added. Then the water sample is poured into the top end of a column containing 1.5 grams of cotton fibers (e.g. cotton balls). The water flows through the fibers in about 1 to 10 minutes (preferably in less than 5 minutes). The flow rate through the fibers is preferably in the range of about 10–100 ml. per minute (and should not be greater than about 200 ml. per minute). More preferably, the flow rate of sample through the fibers is at a rate of about 50 to 100 mL. per minute. It is believed that if the water solution is passed through the fibers at too fast of a rate the complexing agent (with complexed lead) will not have time to become attached to the surface of the fibers.

Although colorimetric techniques are preferred for the determination of the amount of lead present in the sample, other known techniques may be used for the analytical determination, if desired. For example, graphite furnace atomic absorption spectrophotometry is often used to determine parts per billion lead levels. A four stage process is typically involved in the determination. These include drying the sample in a graphite tube, charring the remaining precipitate to remove as much volatile matrix residue as possible, atomization of the analyte for absorption measurement and purging of the tube for the next sample to be tested. It is also possible to use known titration techniques to analytically determine the amount of lead in the sample. Another known analytical technique which may be used is the inductively coupled plasma technique.

In this invention the use of a colorimetric determination is preferred because it can be performed simply and readily in the field by relatively unskilled personnel. The entire testing procedure can be performed in a few minutes, including the time required to obtain the water sample and to extract the lead ions from the water.

EXAMPLE

To 100 ml. of water to be tested there is added 1 ml. of 1.7N nitric acid containing 10% potassium nitrate. The nitrate appears to help pass iron through the filter media and potentially resolubilize any lead compounds. Then 2 ml. of a complexing reagent is added to the sample.

One liter of complexing reagent is prepared using the following ingredients dissolved in sufficient demineralized water to make one liter in volume:

| | |
|---|---|
| Potassium nitrate | 0.080 kg. |
| Tris-(hydroxymethyl) aminomethane | 0.250 kg. |
| Succinic acid | 0.075 kg. |
| Tartaric acid | 0.020 kg. |
| Imidazole | 0.050 kg. |

Two cotton balls are then placed into the barrel of a 60 ml. plastic syringe. A plunger compresses the cotton to the bottom of the barrel. The plunger is then withdrawn.

The water sample is then poured into the top of the syringe barrel. After the flow of water through the syringe stops the plunger is used to squeeze the remaining liquid from the cotton.

Then a clean one inch diameter sample cell is placed under the syringe, after which 25 ml. of 0.04N nitric acid are added to the syringe. The plunger is used to compress the cotton. The volume collected in the sample cell is 25 ml. There is then added to the cell 1 ml. of neutralizer solution.

One liter of the neutralizer solution can be prepared using the following ingredients which are dissolved in sufficient demineralized water to make one liter in volume:

| | |
|---|---|
| Tris-(hydroxymethyl) aminomethane | 0.200 kg. |
| Tartaric acid | 0.020 kg. |
| Sodium hydroxide, 50% w/w | 0.054 kg. |

Then 0.09 grams of indicator reagent are added to the eluted lead solution. The indicator reagent is 2% by weight meso-tetra-(4-N-methylpyridyl) porphine tetratosylate and 98% by weight potassium chloride. The potassium chloride is used as a carrier for the indicator and is not believed to have any role in the lead-indicator reaction. After two minutes the absorbance of the solution at 477 nm. is measured. The lead-indicator complex can then be destroyed with EDTA, after which the absorbance is measured again.

Alternatively, the sample solution may be split into two equal portions, one of which is placed in the colorimeter to test for absorbance directly and the other of which is bleached with EDTA and then tested for absorbance as a reagent blank.

What is claimed is:

1. In a method for extracting lead from a sample of potable water comprising the steps of:
   (a) adjusting the pH of said sample to less than about 4;
   (b) adding to said sample a quantity of complexing agent sufficient to form a complex with said lead in said sample; wherein said complexing agent comprises a dipolar compound selected from the group consisting of tris-(hydroxymethyl)aminomethane, glycine, 2,2-bis(hydroxymethyl)-2,2',2''-nitriloethanol, and 4-morpholineethane-sulfonic acid;
   (c) adjusting the pH of said water to the range of about 6 to 10;
   (d) passing said sample through unmodified cellulosic or siliceous fibers at a flow rate in the range of about 10 to 100 mL. per minute, wherein said fibers are contained in a column, wherein said lead complex is retained on the surface of said fibers; and (e) eluting said lead from said fibers with a weak acid.

2. A method in accordance with claim 1, wherein said fibers comprises cellulosic fibers.

3. A method in accordance with claim 2, wherein said fibers comprise cotton.

4. A method in accordance with claim 2, wherein said fibers comprise paper.

5. A method in accordance with claim 1, wherein said siliceous fibers comprises glass wool.

6. In a method for the quantitative determination of the amount of lead present in a sample of potable water, the improvement which comprises the steps of:

(a) adjusting the pH of said sample to less than about 4;

(b) adding to said sample a quantity of complexing agent sufficient to form a complex with said lead in said sample; wherein said complexing agent comprises a dipolar compound selected from the group consisting of tris-(hydroxymethyl)aminomethane, glycine, 2,2-bis(hydroxymethyl)-2,2',2''-nitriloethanol, and 4-morpholineethane-sulfonic acid;

(c) adjusting the pH of said water to the range of about 6 to 10;

(d) passing said sample through unmodified cellulosic or siliceous fibers at a rate of about 10 to 100 mL. per minute, wherein said fibers are contained in a column, wherein said complex is retained on the surface of said fibers; and (e) colorimetrically determining the amount of lead extracted from said water.

7. A method in accordance with claim 6, wherein said fibers comprises cellulosic fibers.

8. A method in accordance with claim 7, wherein said fibers are selected from the group consisting of cotton and paper.

9. A method in accordance with claim 6, wherein said siliceous fibers comprises glass wool.

10. A method in accordance with claim 6, comprising the further step of eluting said lead from said fibers with a weak acid prior to quantitatively determining the amount of lead extracted.

11. In a method for the quantitative determination of the amount of lead present in a sample of potable water, the improvement which comprises the steps of:

(a) adjusting the pH of said sample to less than about 2;

(b) adding to said sample a quantity of complexing agent sufficient to form a complex with said lead in said sample wherein said complexing agent comprises a dipolar compound selected from the group consisting of tris-(hydroxymethyl)aminomethane, glycine, 2,2-bis (hydroxymethyl)-2,2',2''-nitriloethanol, and 4-morpholineethanesulfonic acid;

(c) adjusting the pH of said sample to the range of about 6 to 10;

(d) passing said sample through unmodified cellulosic or siliceous fibers at a rate of about 20 to 100 mL. per minute, wherein said fibers are contained in a column, wherein said lead complex is retained on the surface of said fibers;

(e) eluting said lead from said fibers with a weak acid, and (f) colorimetrically determining the amount of lead extracted from said water.

* * * * *